(12) United States Patent
Boyce et al.

(10) Patent No.: US 8,321,192 B2
(45) Date of Patent: Nov. 27, 2012

(54) COMPUTER METHOD AND SYSTEM FOR PROMOTING HEALTH, WELLNESS, AND FITNESS WITH MULTIPLE SPONSORS

(75) Inventors: Christopher R. Boyce, Hopkinton, MA (US); Richard M. Boylan, Medfield, MA (US)

(73) Assignee: Virgin Healthmiles, Inc., Framingham, MA (US)

( * ) Notice: Subject to any disclaimer, the term of this patent is extended or adjusted under 35 U.S.C. 154(b) by 428 days.

(21) Appl. No.: 12/553,197

(22) Filed: Sep. 3, 2009

(65) Prior Publication Data

US 2010/0228561 A1    Sep. 9, 2010

Related U.S. Application Data

(63) Continuation-in-part of application No. 11/156,938, filed on Jun. 20, 2005, now Pat. No. 8,027,822.

(60) Provisional application No. 61/191,274, filed on Sep. 5, 2008, provisional application No. 61/100,424, filed on Sep. 26, 2008.

(51) Int. Cl.
*G06G 7/48* (2006.01)
*G01N 33/48* (2006.01)

(52) U.S. Cl. .......................... 703/11; 702/19

(58) Field of Classification Search ................ None
See application file for complete search history.

(56) References Cited

U.S. PATENT DOCUMENTS

| | | | |
|---|---|---|---|
| 6,272,468 B1 | 8/2001 | Melrose |
| 6,850,252 B1 | 2/2005 | Hoffberg |
| 8,027,822 B2 | 9/2011 | Turgiss et al. |
| 2003/0229514 A2 | 12/2003 | Brown |
| 2004/0120557 A1 | 6/2004 | Sabol et al. |
| 2005/0251423 A1 | 11/2005 | Bellam et al. |
| 2007/0015974 A1 | 1/2007 | Higgins et al. |
| 2011/0307311 A1 | 12/2011 | Turgiss et al. |

FOREIGN PATENT DOCUMENTS

WO    WO 2007/134376    * 11/2007

OTHER PUBLICATIONS

Rifkin, D.E., "Electronic Medical Records: Saving Trees, Saving Lives," *JAMA* 285(13):1764, Apr. 4, 2001.
International Search Report and Written Opinion with Notification of Transmittal for PCT/US06/23371.
Office Action from U.S. Appl. No. 11/156,938, mailed on Oct. 16, 2008.

* cited by examiner

*Primary Examiner* — Larry D Riggs, II
(74) *Attorney, Agent, or Firm* — Hamilton, Brook, Smith & Reynolds, P.C.

(57) ABSTRACT

Disclosed is an improved automated system and corresponding computer method of promoting and maintaining health, wellness, and fitness. Multiple sponsors per member participant are enabled. Each sponsor defines respective qualifying healthy behavior (activities, purchases, other) and reward rate for each such activity and purchase. A rewards engine operates on member accounts adding units per member completion of qualifying healthy activities or purchases, thereby encouraging members to adopt healthy habits. This, in turn, leads to better health, wellness, and fitness for the subject members. The combination of different and multiple sponsors having different qualifying activities/purchases provides increased member incentive.

20 Claims, 8 Drawing Sheets

COMPUTER METHOD AND SYSTEM FOR PROMOTING HEALTH, WELLNESS, AND FITNESS WITH MULTIPLE SPONSORS

RELATED APPLICATIONS

This application claims the benefit of U.S. Provisional Application No. 61/191,274, filed Sep. 5, 2008, and of U.S. Provisional Application No. 61/100,424, filed Sep. 26, 2008. This application is also a continuation-in-part of U.S. application Ser. No. 11/156,938 (now U.S. Pat. No. 8,027,822), filed Jun. 20, 2005, by common assignee. These patent applications are herein incorporated by reference in their entireties.

BACKGROUND OF THE INVENTION

Various automated systems exist for promoting and maintaining health and wellness. Some of these systems are directed to healthcare data management used by heath care professionals, patients, or both. Of the healthcare data management systems, some monitor and record vital statistics.

Other automated systems are directed to fitness and monitoring of healthy behavior and activities. Some form of measuring and monitoring biometrics is typical in these systems. Such systems are used by, for example, fitness professionals, physical therapists, trainers, etc. Some fitness programs provide incentives or rewards to the patient participant for reaching certain milestones.

A high percentage of the initial use of the forgoing systems is curative in nature, e.g., recovering from or otherwise responding to an illness or injury. Lacking is an automated system that promotes a preventative approach to health, wellness, and fitness. Also lacking are such systems with widerspread sponsorship beyond healthcare and fitness professionals.

SUMMARY OF THE INVENTION

Embodiments of the present invention provide an improved computer-based system and corresponding computer method of promoting and maintaining health, wellness, and fitness. Embodiments of the present invention are based on a preventative health maintenance approach and employ multiple sponsors per member participant. In particular, Applicants have discovered that participants (members) in such preventative health, wellness, and fitness programs have greater success when there are built-in incentives. The greater number of sponsors, the greater number of opportunities for incentive rewards. Thus, embodiments of the present invention increases both the frequency and number of different types of occasions for earning incentive rewards (in the aggregate across multiple sponsors).

In a preferred embodiment, the invention method and system include: an online portal; a sponsor data store; a member data store; and a rewards engine.

The sponsor data store holds sponsor data. For each sponsor, the data store indicates a list of members (by name, member number, or other identifier), activities or purchases that the sponsor qualifies or defines as healthful behavior, and the reward rate for each such activity or purchase.

The sponsor data store may cross-reference members by policy number, frequent shopper identifier, and the like.

The member data store stores member account information, and the rewards engine tracks and accumulates units credited to the member by different sponsors for different activities. The rewards engine operates on the member accounts by adding and subtracting units per member activity as logged into the system by the members (via user-interactive interface to the online portal) and by respective data feeds from the sponsors as detailed below.

The rewards engine is responsive to input data that effectively indicates qualifying healthy activity completed by subject members. The rewards engine uses the sponsor data as stored in the sponsor data store to determine a number of units to add to the respective member account of the subject member for the completed healthy activity. The respective member account accumulates units awarded to the subject member by different sponsors for different qualifying healthy activities at an increased potential due to multiple potential sponsors, thereby promoting participation in healthy activities by the members.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Incorporated herein in its entirety is U.S. patent application Ser. No. 11/156,938, now U.S. Pat. No. 8,027,822, which describes a global computer network-based interactive health, wellness, and fitness management system. The present invention provides improvements in that system.

Figure 1:
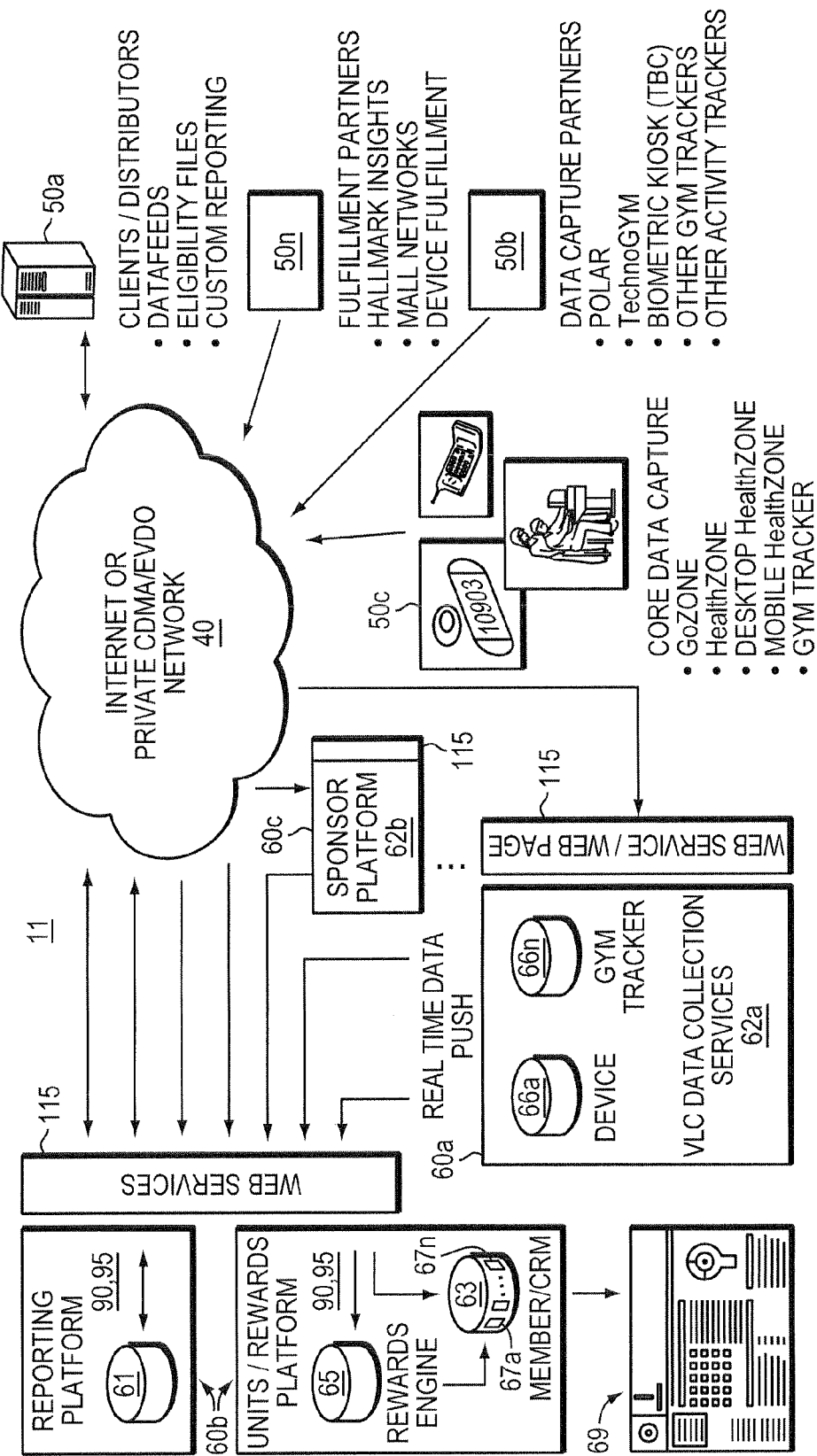
FIG. 1 is a schematic view of a computer network and system embodying the present invention.

FIG. 1 illustrates a user interactive health, fitness, and wellness management system 11 that embodies the present invention. The system 11 is formed of: (a) a member data store 63 that stores member accounts 67a, b, . . . , n (generally 67) with corresponding process modules that operate on, maintain, and/or retrieve data from the member data store 63; (b) a sponsor data store 61 with corresponding process modules that operate on, maintain, and/or retrieve data from the sponsor data store 61; (c) a rewards engine 65; and (d) multiple sponsor/device data collection platforms 62a, b, . . . , n (generally 62) on respective servers 60a and 60c. The system may also include a portal 69 hosted by a server 60b.

Members and sponsors (not shown) interact with the system 11 via clients 50a, b, . . . , n (generally 50) connected to the servers 60a-60c (generally 60) via a communications network 70 (e.g., the Internet). Data exchangers 115 coupled to the servers 60 and the network 70 make it possible to exchange information among the various data stores 61, 63, 65, the data collection platforms 62, and the clients 50. For example, the data exchanger 115 may enable members to access and/or update their accounts 67 on the data store by accessing the portal 69 with a client 50a.

The member data store 63 stores member data and member account information for each member. In some embodiments, the member data is split between sensitive data and other data, and stored in separate respective data stores for security (privacy) purposes. Each member has an account 67 that stores or otherwise holds units credited to the member by different sponsors for different activities. The rewards engine 65 operates on the member accounts 67, adding and subtracting units per member activity as logged into the system 11 by the members (via user-interactive interface to the online portal 69 and device data feeds (trackers) 66a-66n (generally 66)) and by respective data feeds from the sponsors (via sponsor platforms 62b) as made clear below.

The device data feeds 66 (or device data trackers) are used to collect information from a variety of sources, including, but not limited to, gyms, retailers, and healthcare providers. For example, the device data trackers 66 may be used to gather information related to physical fitness, such as workout regimen or blood pressure, or information about spending and eating habits, such as supermarket or restaurant purchases. Further details of the data trackers 66 (including gym/health club tracking devices) and upload of data captured by the data trackers 66 through data collection platforms 62 may be found in U.S. patent application Ser. No. 11/156,938, now U.S. Pat. No. 8,027,822 by assignee herein incorporated by reference.

The sponsor data store 61 holds sponsor data for multiple sponsors, such as employers, health clubs, insurers, retailers, manufacturers, government entities, healthcare profession service providers, and pharmaceutical entities. For each sponsor, the data store 61 indicates: (i) a list of members (by name, member number, or other identifier); (ii) activities or purchases that the sponsor qualifies or defines as healthful behavior; and (iii) the reward rate for each such activity or purchase. The sponsor data store 61 may cross-reference members by policy number, frequent shopper identifier, and the like.

Embodiments of invention system 11 enable, for example, four categories of sponsors, namely corporate sponsors, health club sponsors, insurers (health, life, disability), and retail sponsors. Other sponsors may include government entities, healthcare professionals, pharmaceutical entities, and so forth. Retail sponsors include retail sales entities (e.g., department stores), grocers, and the like. Sponsors access and communicate with invention system 11 through interactive interfaces (portals 69) on respective clients 50.

Each member-participant can interact with the system 11 through a client 50 (e.g., client 50a). As described above, each member has an account 67 that accumulates units from healthful behavior. Different sponsors deem respective activities to qualify as good health behavior and define (set) the number of units the system 11 is to use to reward each such activity when completed by a member. As the member account 67 accrues units over time, certain thresholds or total unit limits that define respective membership/reward tiers or levels with corresponding member benefits are reached. For example, 0 through 199 units in a member account 67 defines a first member-reward tier or level 1 in the system 11. A member account 67 holding between 200 and 299 units is a second member-reward tier or level 2 account with respective member benefits. A member account 67 holding between 300 and 399 units is a third member-reward tier or level 3 account with respective member benefits; and so on.

The units held by a member account 67 have a cash equivalent. The invention system 11 enables corporate and other sponsors to give cash rewards for each increase in member-reward tier/level achieved by a member 34. Further, as a function of member-reward tier/level, the invention system 11 enables retail sponsors to give additional units to a member account 67 for purchases the member makes at the retailer sponsor (i.e., units equivalent of a percentage of the purchase price with higher percentages for higher member-reward tiers/levels). This graduated scale rebate model and other features of the present invention are further detailed below.

Next an example is discussed with reference to FIGS. 1 and 3 for purposes of illustration and not limitation of embodiments of the present invention. A member 34 has his employer as a corporate and first sponsor in invention system 11. A health club is a second sponsor of the member 34 in system 11. A health insurer is a third sponsor and a retailer is a fourth sponsor. Note the different and multiple sponsors enable a wide variety of ways (e.g., activities, purchases, etc.) for the member 34 to earn or otherwise obtain units. In this way, there is increased opportunity followed by increased rate of accumulation and thus increased incentive, thereby promoting healthy behavior of the member 34.

The employer company (corporate sponsor) credits the member account 67 (by way of a group health insurance rebate, employee benefit, other arrangement and the like) $300 per year, for example, for achieving a system (member-reward) level 5, or a respective percentage for achieving each of member-reward levels 2 through 4. The corporate sponsor credits the member account 67 for different preventative health activities (e.g., exercising, yearly physical, etc.), company cafeteria healthy food purchases, and/or other company sponsor deemed good health activities and behavior. These qualifying activities and rate of reward in units are defined in corporate sponsor records in sponsor data store 61.

For purposes of crediting the member account 67, the member 34 logs into portal 69/system 11 through a client 50 and enters completed activity data through the interactive user-interface. In addition, the member 34 through portal pages/sponsor platforms 62a may upload data that was captured through one or more devices (e.g., system pedometer, etc.). In one embodiment the uploaded device activity data is transmitted to the rewards engine 65 using real-time data push technology. Point-of-sale data is also fed into system 11. The rewards engine 65 verifies the received (input) activities data with corporate sponsor records and definitions in the sponsor data store 61, determines the number of units to be added to the member account 67, then adds the calculated number of units to the member account 67.

The Health Club sponsor may reward the member for achieving the different member-reward levels or tiers. In one example, the Health Club sponsor awards free apparel to the Level 1 member, a free guest pass for Level 2 member, a free personnel training session to the member achieving Level 3, and the like. The sponsor data store 61 stores information regarding this reward program as defined by the Health Club sponsor. The invention system 11 (through portal 69 and client 50) enables the Health Club sponsor to check on (view) member account 67 unit totals for purposes of this step level reward program/plan. In some embodiments, the system 11 uses pertinent sponsor data store 61 records and sets an alert or similar automated message to the Health Club sponsor. When the member account 67 reaches a threshold amount (as defined in sponsor data store 61 by the sponsor), the system 11 triggers an alert message to the Health Club sponsor, for example, by posting the message to a portal 69 screen view displayed to the Health Club sponsor at login or other times.

Further, the Health Club sponsor issues a system-generated voucher to a member for participating in or completing certain classes or sessions. The Health Club may purchase and generate vouchers from system 11 portal 69 in bulk (optionally in advance) or on an as-need basis. The Health Club sponsor may chose to be billed for the vouchers on generation or on member redemption. Each voucher has a unique identification code tracked by the invention system 11 (rewards engine 65). The Health Club sponsor also indicates to the system 11 the number of units to credit a member account 67 per class, session, or activity. A record of these and other Health Club sponsor defined (qualified) activities and respective reward rates are stored in sponsor data store 61.

Once the Health Club issues the voucher to a member, the member (e.g., via client 50c) logs onto portal 69/system 11 and enters the voucher identification code along with particulars, e.g., the name of Health Club sponsor who issued the voucher, the dates/times of class/sessions completed corresponding to the voucher, and the like. The rewards engine 65 (a) validates the voucher by identification code, the issuing Health Club, and class/session, and (b) credits the respective member account 67 with number of units the Health Club sponsor has attributed (assigned or the otherwise predefined and stored in sponsor data store 61) for the corresponding class/session.

The foregoing vouchers may be used by other sponsors (of all categories) to reward members for specific activities beyond a respective core program of the sponsor. The sponsor may use the voucher to reward a member with additional units for the member account 67 and/or with a cash equivalent. For example, a sponsor may use a voucher to reward additional units to a member for completing an annual physical, for completing a particular class/session, for completing a sponsor-defined/qualified activity, for purchasing a sponsor-defined healthy meal option at participating cafeterias, and the like. These additional awards help accelerate the member through the different member account tiers/levels of system 11. In turn, this improves member engagement and program compliance. See below for more details on vouchers.

Use of vouchers is not mutually exclusive of other means for rewarding units. Sponsors may still reward units and cash equivalents using direct data feed, as described below.

Returning to the example different sponsors of the member 34, the Health Insurance Sponsor may reward (pay) $130.00 to the member in a given year for achieving a certain member-reward tier/level. The Health Insurance Sponsor rewards respective units for performing certain activities, such as completing a yearly physical. Each of these qualifying events/activities is defined or otherwise indicated in respective sponsor records of the sponsor data store 61.

To record these activities, the member 34 may log onto the system 11 via the portal 69 and enters member name, health insurance policy number, and description of activity completed. The interactive health, fitness, and wellness management system 11 in turn asks the Health Insurance Sponsor (through respective client 50 communications) to validate the policy number and corresponding member name. Upon Health Insurance sponsor validation, the rewards engine 65 credits the member account 67 according to qualifying activities and reward rates stated (predefined or preset by the sponsor) in the sponsor record of sponsor data store 61.

The Retailer sponsor classifies certain goods as "healthy" and awards respective units for each purchase of such goods by the member. The retailer sponsor (at client 50) through portal 69 sets these and other reward rates and qualifications in a respective record stored in sponsor data store 61. Subsequently (such as on a weekly basis), the retailer sponsor supplies to System 11 point of sales or purchase data. The rewards engine 65 parses the received data and determines number of units to credit the member account 67 following the qualifications and reward rates preset by the sponsor and stored in sponsor data store 61.

Interactive Health, Fitness, and Wellness Portals

Figure 2:
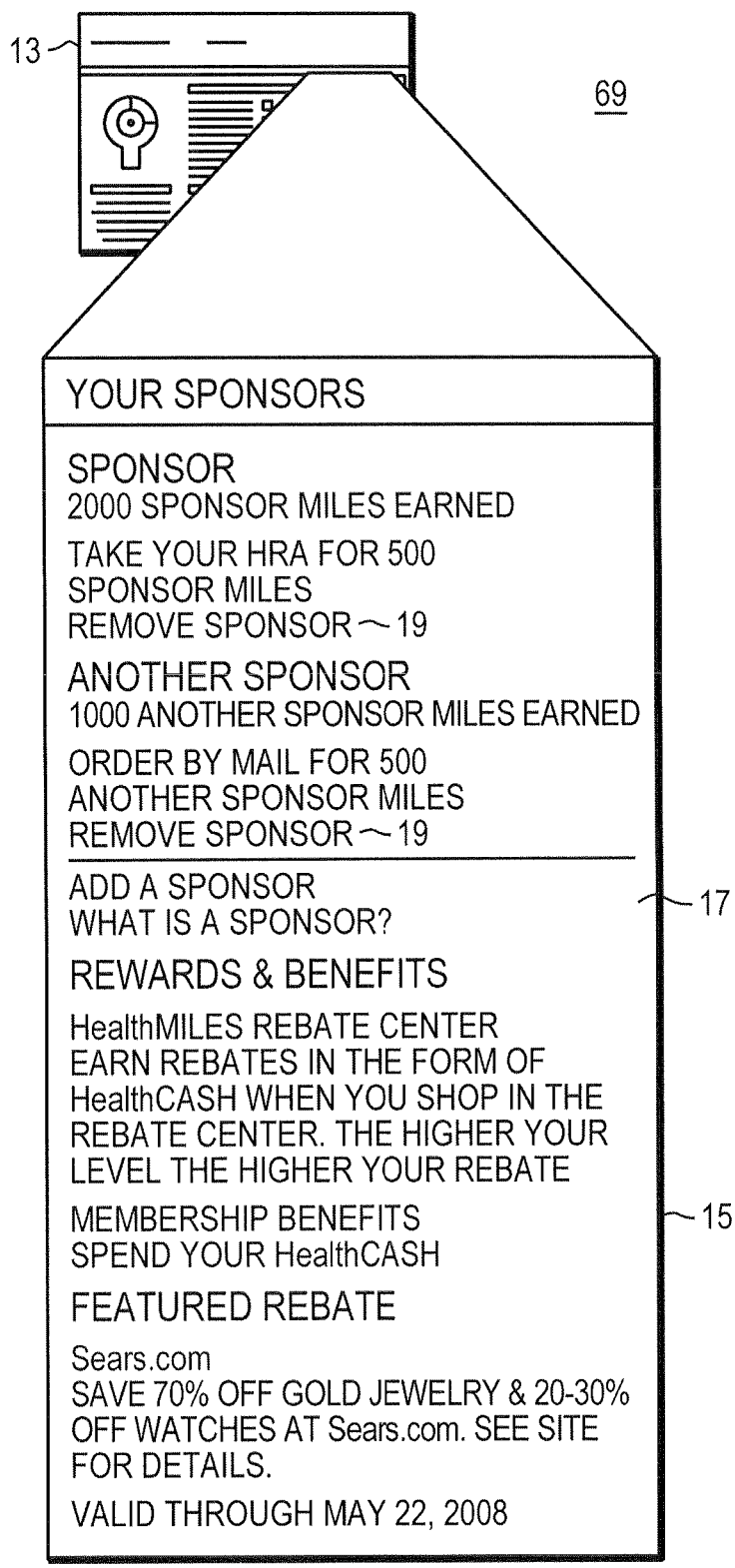
FIG. 2 is a schematic illustration of a screen view in the user-interface of embodiments of the present invention.

FIG. 2 shows a screen view of the portal 69 according to embodiments of the present invention. Screen views 13 of the portal 69 show sponsor information, including, but not limited to sponsor name, sponsor rewards earned (e.g., "2000 Sponsor Miles earned"), and qualifying activities (e.g., "Take your Health Risk Assessment (HRA) for 500"). The screen view 13 may also provide information related to rebates, including a featured rebate promotion, and information about how the system 11 works. In some embodiments, the system 11 enables members 34 to add, delete and/or change sponsors through the user-interactive interface of portal 69 as shown at 17 and 19 in FIG. 2. The portal 69 may include various other pages and menu options that members can use to enter or download additional data.

The system 11 also enables sponsors to display respective logos in portal screen views 13 to members, to promote respective rewards, and to provide links to external web pages via the portal 69. For example, the system 11 may enable sponsors to customize the respective portions of the portal pertaining to rewards or rebates for members. Sponsors may also be able to selectively promote rewards, rebates, and the like to specified members via the portal 69. Sponsors, like members, may have unique login credentials and may use various pages and menu options to upload, download, or otherwise exchange data.

Frequent Shopper Programs

Frequent shopper programs of the retail sponsor may be combined with the interactive health, fitness, and wellness system 11 shown in FIG. 1. For every n dollars spent as a frequent shopper, the member earns a unit in the system 11. The retail sponsor may set the ratio of dollars spent to member account units earned. The ratio is stored in the respective sponsor record in sponsor data store 61. The invention system 11 (i.e., sponsor data store 61) cross references a retailer-issued frequent shopper identifier with a system 11 member identifier or member account 67. The rewards engine 65 uses the foregoing information from sponsor data store 61 when processing point-of-sale (POS) data and when determining the number of units to credit to the member account 67.

Further embodiments of invention system 11 accommodate multiple retail sponsors of the same type as follows. For example, say there are three major grocers, grocer 1, grocer 2, and grocer 3. Per respective grocer agreements (arrangements) as recorded in the sponsor data store 61, for every $1.00 that the member spends at grocer 1, the member accumulates one unit his respective member account 67. For every $2.00 that the member spends at grocer 2, the member account 67 earns one unit. For every $3.00 that the member spends at grocer 3, the member account 67 earns one unit.

The member specifies (through portal 69) to invention system 11 (and rewards engine 65) that he is a frequent or preferred shopper program participant at one of these grocers and selects that grocer as the exclusive grocer sponsor for purposes of the invention system 11. In turn, the system 11/rewards engine 65 credits the member account 67 at the corresponding rate of the member-selected grocer according to the grocer sponsor records in sponsor data store 61. The system 11 also allows the member (via portal 69) to subsequently change grocer sponsor. Indication of the member's current grocer sponsor is maintained in member data store 63 records and/or sponsor records in sponsor data store 61.

Figure 3:
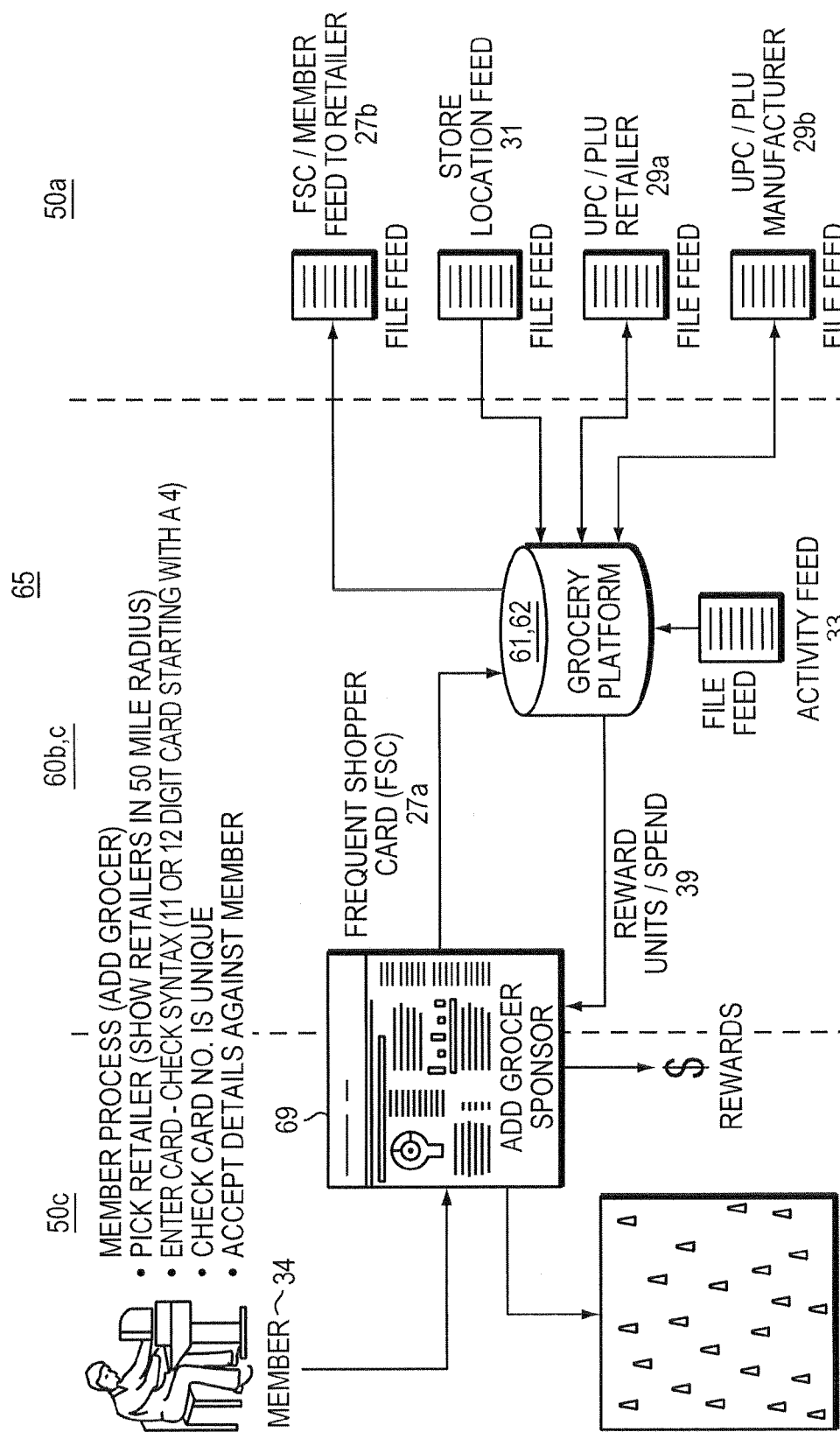
FIG. 3 is a flow diagram of one embodiment of the present invention rewards engine processing member account credits from multiple sponsors.

FIG. 3 shows file feeds and other data transfers (generally 29, 31, and 33) used to accomplish the foregoing sponsor rewards across multiple sponsors to respective sponsor platforms 62 of invention system 11. Initially, a member 34 (at client 50c) operates the portal 69 process for adding a grocer sponsor for example. Other sponsors may similarly be added. Based on member address/location data in member data store 63 and on sponsor addresses and type in the sponsor data store 61, the system 11 provides a display 30 of qualifying local grocers to the member 34. The member 34 selects the listed grocer that he frequents and for which he has a frequent shopper card (program membership). The user enters the grocer supplied frequent shopper card/program identification number (step 27a), which the rewards engine 65 verifies for uniqueness in system 11 and for accuracy with the grocers records (step 27b) at client 50a. Upon verification, the invention system 11 records the frequent shopper identification data in member data store 63 records for member 34.

The subsequent shopping activity by member 34 at the selected qualifying grocer sponsor produces program activity data. This data is captured by the grocer sponsors system (client 50a) and provided to invention system 11 in various file feeds 29, 31, 33. Each file feed 29, 31, 33 in one embodiment preferably follows a comma-separated variable (.csv) data file format indicating: (i) member identifier or name; (ii) number of units being rewarded; and (iii) reason for reward. Alternatively, the indication of number of units may refer or default to reward rate per activity in sponsor records of sponsor data store 61.

If a sponsor supplies to the system 11 purchase data such as POS data files 31, 33, then the system 11/rewards engine 65 filters the received POS data by member identification of members listed in member data store 63. The member identification filter may first be by frequent shopper identification issued by the sponsor and cross-referenced to the invention system 11 member identification in member data store 63. Next, the rewards engine 65 filters sponsor activity data by product code (e.g., UPC, PLU, other) 29a, special sponsor product code (e.g., star system), SKU number, manufacture/brand 29b, or the like.

The resulting filtered data from the sponsor platform 62 indicates qualifying member and qualifying total purchase dollar amount on which to base the current reward. The sponsor platform 62 parses the data feed formatted data 31, 33 and filtered data 29a, b and enables the rewards engine 65 to properly credit the member accounts 67 (step 39). In particular, the rewards engine 65 matches the named member in the subject data to a respective member account 67, and verifies number of units to add 39 to the member account 67. For the filtered POS data 31, 33, the rewards engine 65 uses the qualifying total purchase dollar amount received and applies a multiplier (reward rate) defined by the sponsor in sponsor data store 61. The outcome is the number of units that the rewards engine 65 adds to the member account 67.

Rebate Features

Turning to the rebate feature of embodiments of the invention system 11, the portal 69 enables online retail shopping at certain retailers. A screen view of the portal 69 displays a product offer with an indication of a percent markdown or rebate for qualifying items. The screen view includes a hyperlink or other connection to the retailer's on-line shopping site.

The level or tier of the member account 67 gauges the effective percent markdown or rebate for the qualifying item. Thus, the percent markdown/rebate is on a graduated scale in some embodiments.

In particular, a Level 5 member may take advantage of the full markdown percent advertised, while a lower level member will only be allowed a respective portion of the advertised markdown percent. The markdown percent of the qualifying item purchase price is awarded in system 11 units (i.e., the number of units whose cash equivalent equals the markdown percent dollar value $A = M \times P$, where M is the effective markdown percent per member level and P is the qualifying item purchase price).

Once a member completes a purchase (of the qualifying item) at a retailer site as linked through the portal 69/system 11, the rewards engine 65 determines the rebate in number of units (above calculation) and credits the respective member account 67.

Such rebates further add to the variety of opportunities for a member to earn units for his member account 67. The rebates being tied to member-reward level or tier of the member account 67 motivates and provides incentive for the member to make healthful choices and engage in healthy activities that earn units and cumulatively achieve higher member-reward levels/tiers in system 11.

Computer Methods for Promoting and Maintaining Health, Wellness, and Fitness

Figure 4:
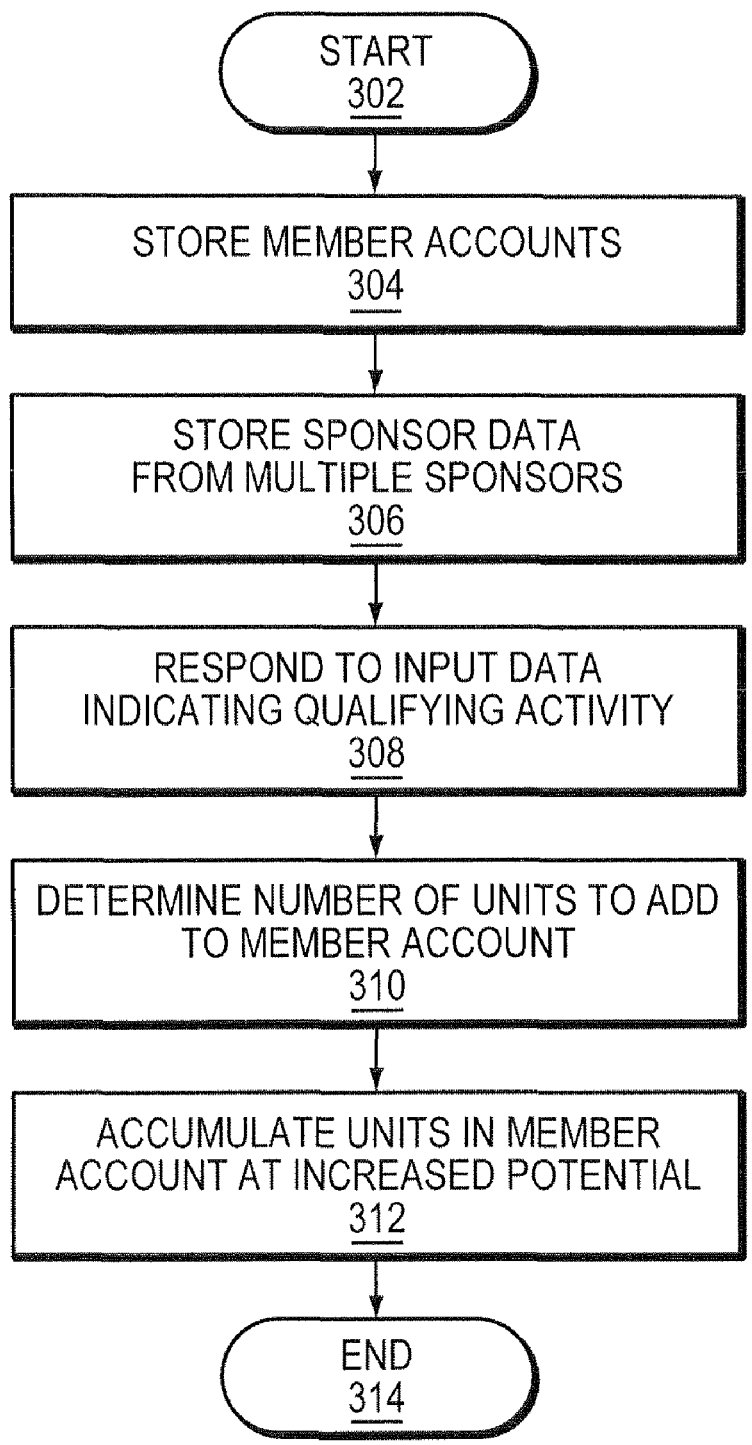
FIG. 4 is a flow diagram of a computer-based interactive health, wellness, and fitness process according to embodiments of the present invention.

FIG. 4 is a flow diagram of an interactive computer-based method for promoting and maintaining health, wellness, and fitness. The method starts (step 302) with storing information about members (step 304), including a member account for each member, in a member data store, such as the data store 63 shown in FIG. 1. Similarly, sponsor data from multiple sponsors is stored (step 306) in a sponsor data store (e.g., sponsor data store 61). The sponsor data includes indications for each sponsor of (i) qualifying members; (ii) qualifying healthy activities for which qualifying members are to be rewarded; and (iii) reward rate for each qualifying activity.

At step 308, a rewards engine (e.g., rewards engine 65) responds to input data that effectively indicates qualifying healthy activity completed by a subject member. Next, at step 310, the rewards engine uses sponsor data to determine a number of units to add to the respective member account of the subject member for activity completed by the subject member. Then, at step 312, units awarded to the subject member are accumulated in the respective member account by different sponsors for different qualifying healthy activities, thereby promoting healthy behavior among members. This accumulation occurs at an increased potential because the method involves many potential sponsors. Finally, the process ends at step 314.

Figure 5:
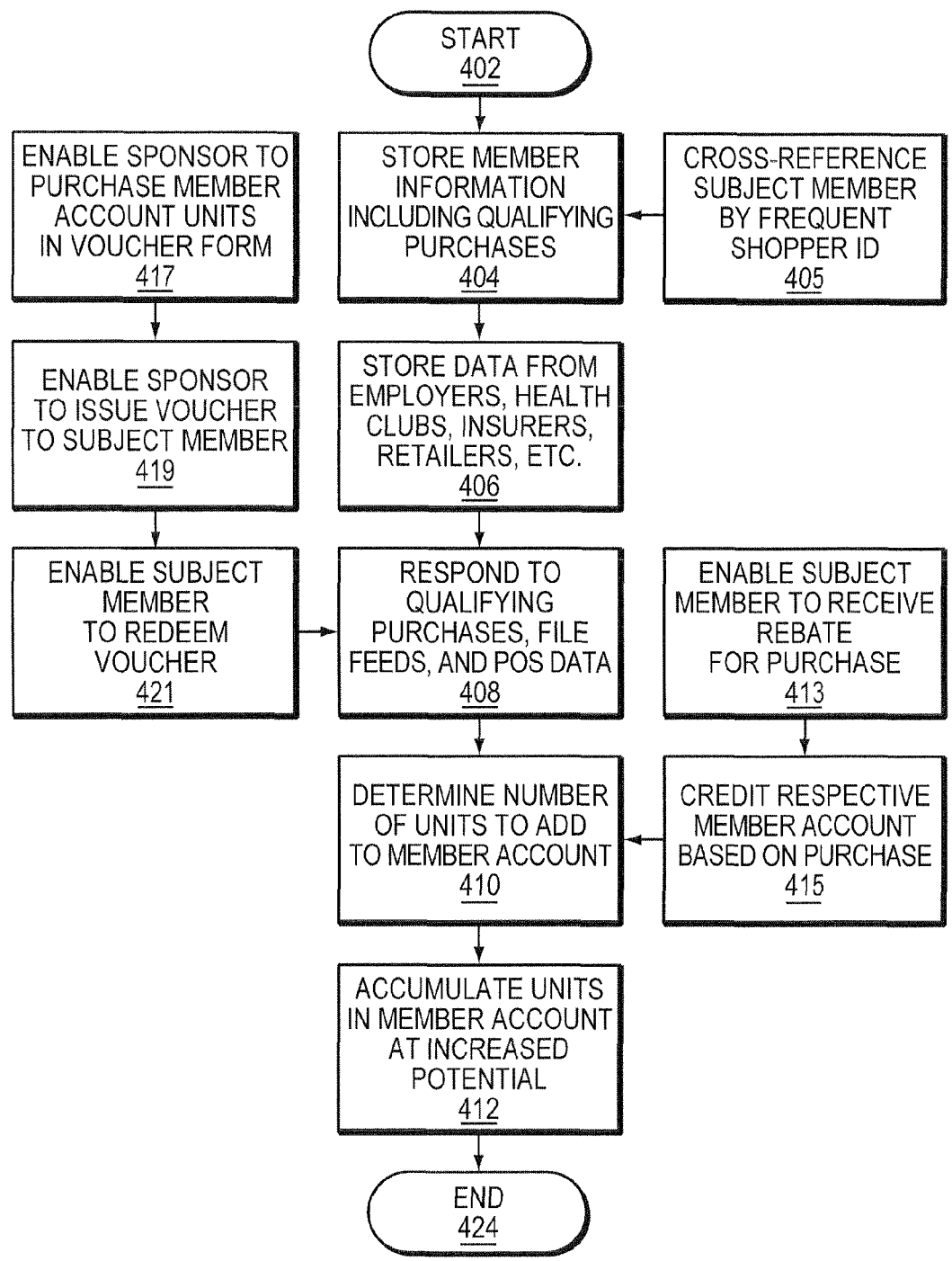
FIG. 5 is a flow diagram of a computer-based interactive health, wellness, and fitness process according to alternative embodiments of the present invention.

FIG. 5 is a flow diagram of an alternative interactive computer-based method for promoting and maintaining health, wellness, and fitness. The process begins (step 402) with storing member information, including qualifying healthy purchase information (e.g., diet food instead of junk food), in respective member accounts (step 404). The member information is cross-referenced (step 405) with frequent shopper identification numbers from a frequent shopper program for a retailer that sponsors the process. Next, data from employers, health clubs, insurers, and retailers, including reward rate information, is stored (step 406) in a sponsor data store.

At step 408, a rewards engine responds to data representing qualifying purchases by members, file feeds from sponsors and members, and POS data from sponsors. This data is used to determine (step 410) the number of units to add to the member account based on the qualifying data from step 408 and in response to rebates, which the process enables subject members to receive for purchases from retail sponsors (step 413). These rebates are then credited (step 415) to the member's account based on the purchase. Next, the rewards engine determines (step 410) how many units to add to the member account based in part of the items purchased at the retail sponsors. Certain items may be linked to specific benefits, rewards, or numbers of points based on the frequent shopper program. The units are then accumulated in the member account (step 412) at increased potential before the process ends (step 424), thereby encouraging members to adopt and maintain healthy purchasing and eating habits.

The alternative process allows shown in FIG. 5 also includes a voucher subprocess that enables sponsors to purchase member account units in voucher form (step 417). The sponsor can then issue the vouchers to subject members (step 419) upon completion of healthy activities, as promotions, or for meeting other criteria. For example, a Health Club sponsor may award vouchers to subject members who participate in exercise classes or lose a given amount of weight. The subject members can then redeem the vouchers at their convenience (step 421). Thus, in this embodiment, the sponsor does have to enter data concerning completion of healthy activity. Instead, the sponsor gives pre-made vouchers to subject members, who may trigger the rewards engine 65 by entering a corresponding voucher code at home using the portal 69.

Voucher Processes

Figure 6:
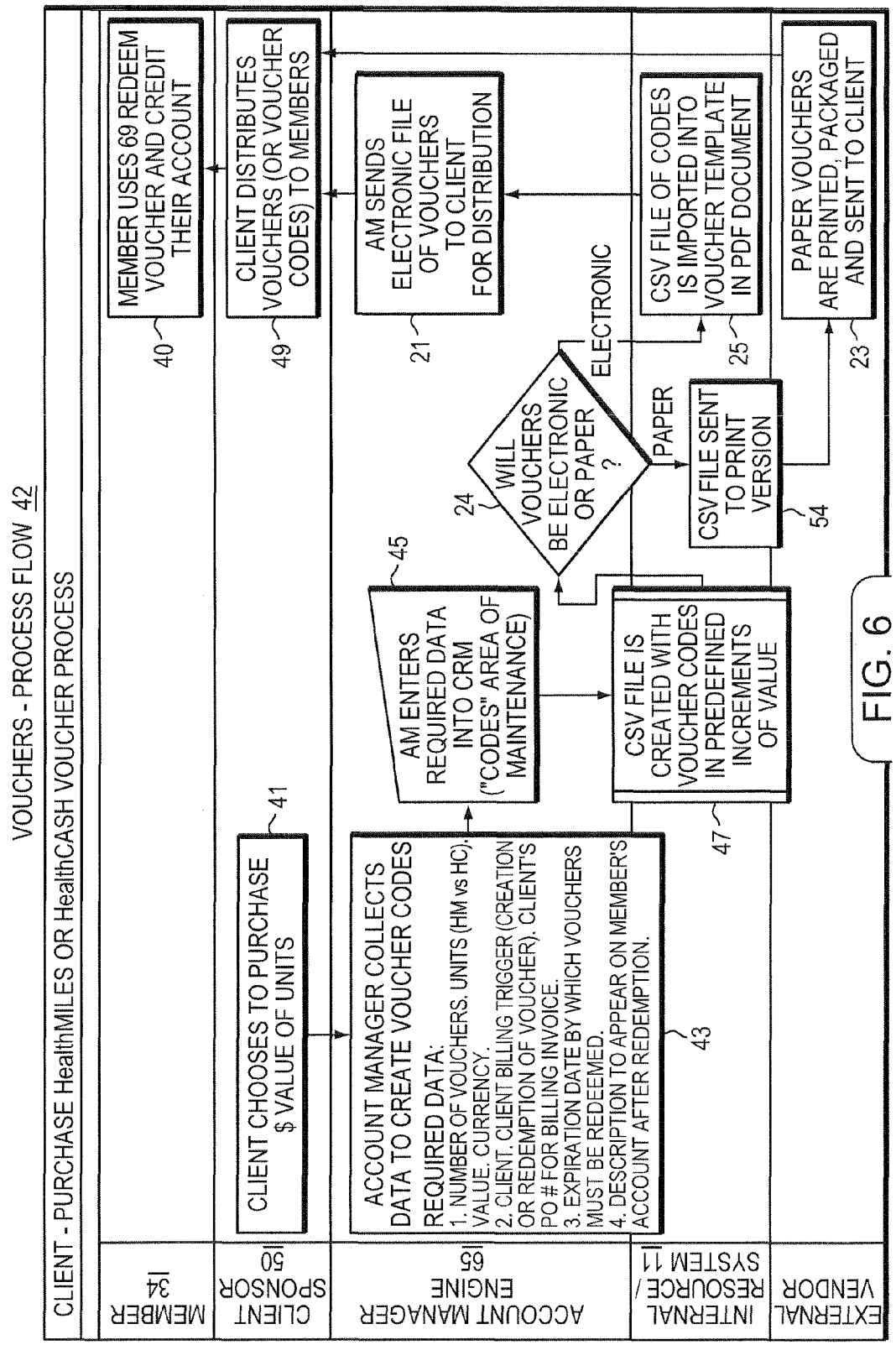
FIG. 6 is a flow diagram of voucher generation and redemption in embodiments of the present invention.

FIG. 6 is a diagram that shows one embodiment of an inventive voucher process 42 in detail. A sponsor operating and interacting with system 11/portal 69 through client 50 chooses to purchase units (i.e., the dollar equivalent thereof) for awarding to member accounts 67 (step 41). In response to this sponsor request, the rewards engine 65 interactively collects data from the sponsor client 50 to create voucher codes (step 43). The data may include, for non-limiting example:

number of vouchers requested by the sponsor;
number of units and corresponding value per voucher (this enables voucher values to be customizable by batch);
indication of currency to print on the voucher (e.g., system units, cash equivalent or other);
sponsor name, purchase order number (optional) and billing trigger (creation or redemption of voucher);
expiration date by which vouchers must be redeemed; and description to appear on member account after redemption.

Next, having received/collected the necessary data, the rewards engine 65 enters (step 45) this data into a codes maintenance area (e.g., application) of system 11. In response, system 11 (at step 47) creates a .csv file with voucher codes for vouchers in the sponsor requested/pre-defined increments of value. These voucher codes and resulting vouchers are assigned to the specific sponsor.

At decision juncture 24 based on sponsor input, the system 11 determines whether the vouchers are to be issued in paper form or electronically. If paper form is requested by the sponsor, then system 11/step 54 sends the .csv file to a print vendor. There the paper vouchers are printed, packaged, and sent to the sponsor (step 23) for distribution to members (step 49).

If the vouchers are to be in electronic form, system 11 at step 25 imports or otherwise merges the .csv file of voucher codes into a voucher template. This includes adding sponsor branding and/or other design details. Step 25 results in a .pdf document containing the subject vouchers. The rewards engine 65 at step 21 sends the electronic (.pdf) file of vouchers to the sponsor-client 50 for distribution to members (step 49).

The sponsor distributes the vouchers or voucher codes to members accordingly (step 49). To redeem a voucher (step 40), a member uses the interactive portal 69 entering voucher code, etc., as described previously. In turn, rewards engine 65 validates the voucher code and either triggers the respective reward to the members account 67 or gives an error (i.e., voucher already redeemed, voucher expired, code not valid, etc.). Each voucher code can only be used and/or redeemed once.

Reward, Voucher, and Rebate Funding

Embodiments of the invention system 11 are funded by membership fees, sponsor agreements/arrangements, voucher sales and retailer rebate agreements. For example, a grocer sponsor pays three cents into the invention system 11 for every $1 spent by a member at the grocer's store. This is a sufficient margin where the cash equivalent payout by system 11 is one cent for every one dollar spent by a member at the grocer's store. Similarly, voucher prices as paid by sponsors provide additional revenue. The cost structure of voucher programs per given sponsor is controlled by dollar equivalent of member-account units set by system 11.

Data Communications Tiers

Figure 7:
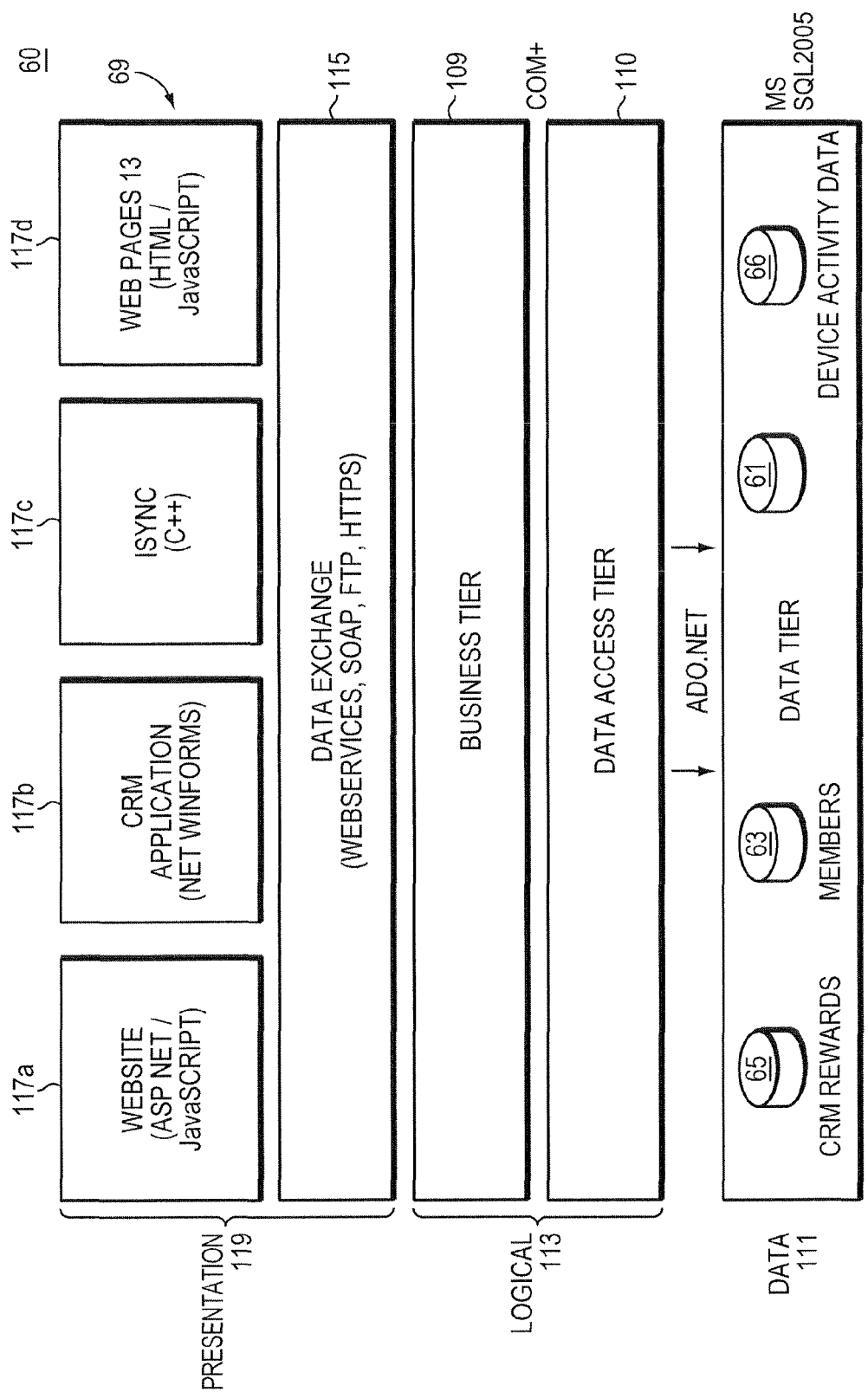
FIG. 7 is a block diagram of data and communication layers in the embodiment of FIG. 1.

FIG. 7 shows three levels, or tiers of data communications and controls used in the communications network 70 of the interactive health, fitness, and wellness system 11 shown in FIG. 1. A data layer 111 or tier is the lowest level and supports data stores 61, 63, 65, 66, which may be relational databases in structured query language (SQL) or any other suitable query language. The data layer 111 may use a set of classes, such as ADO.NET, to connect the data stores 61, 63, 65, 66 to data-sharing consumer applications, such as applications residing on other tiers or accessible via the clients 50 or the portal 69. Suitable classes allow the consumer applications to retrieve, manipulate, and update data, including data related to member and sponsor accounts. Suitable classes support a variety of development needs, including serving up data to the user interface and middle-tier business logic methods used by applications and tools.

Next is a (business and application) logic layer 113 supported by component services (COM+) or similar enterprise wide programming model. The logic layer 113 handles resource management tasks, such as thread allocation and security, in addition to making applications more scalable by providing thread pooling, object pooling, and just-in-time object activation. The logic layer 113 also helps to protect the integrity of member and sponsor data by providing transaction support, even if a transaction spans multiple data stores over a network. The logic layer 113 may include one, two, or more data processing tiers and components, each with respective functionality shown through one or more interfaces. Common or standard middle tier/business logic layer techniques are employed.

In the illustrated example, the logic layer 113 is formed of a data access tier 110 and a business tier 109. This is the business logic 109 that drives the application processes. Basically this is the process and rules around what happens when a user makes a functional request via the application. The data access layer 110 is the code that drives what data it needs to support the logic requirements in the business logic. Techniques known in the art are used to implement these processes and operations.

A presentation layer 119 forms the third tier or level of network data communications and control. The presentation layer 119 is formed of (a) a data exchanger 115 and (b) one or more applications 117a, ..., n (generally 117) executing and supporting operations of the invention portal 69 (FIGS. 1 and 2) described above. The data exchanger 115 interfaces between tiers of the logic layer 113 and the applications 117. The data exchanger 115 provides web services and security protocols/control for data access (e.g., from data layer 111 and data processing/component results of logic layer 113) by applications 117. Other configurations are suitable as well.

Applications 117 include, for example, the member operations and various sponsor operations, e.g., voucher generation and redemption (process 42, FIG. 6), rewards and rebate processing (FIGS. 4 and 5), sponsor deletion and addition (FIG. 2), and rewards account viewing (FIG. 2), and online shopping, among other operations and portal activities.

Network Architecture

Figure 8:
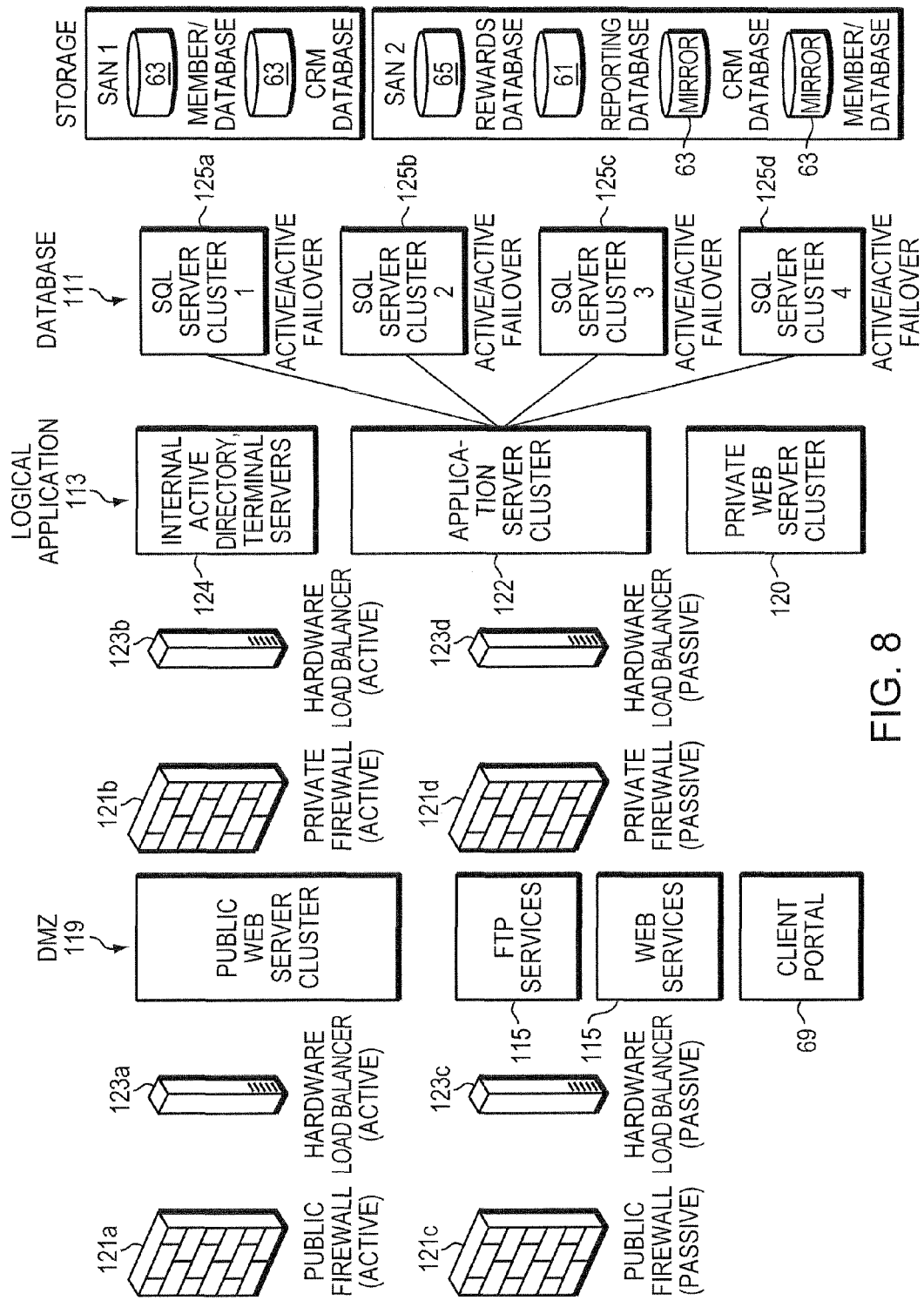
FIG. 8 is a schematic view of the computer network architecture of the embodiment of FIG. 1.

FIG. 8 shows how elements of the interactive health, fitness, and wellness system 11 of FIG. 1 are configured for data communication in the network architecture of FIG. 7. Other configurations and architecture are suitable as well. In the FIG. 8 embodiment, (active and passive) public firewalls 121*a, b, c, d* and (active and passive) load balancers 123 *a, b, c, d* are employed between clients 50 and servers 60 of the invention system 11 as well as between the presentation layer 119 elements (e.g. client portal 69, web services/FTP services 115, etc.) and the logical layer 113. Further, the logical layer 113 employs a private global network server cluster 120, an application server cluster 122, and other internal components 124 (e.g., active directory, terminal servers, etc.) following the COM+ standard. The data layer 111 employs relational data stores 61, 63, 65, mirrors thereof as needed, and pertinent query server clusters 125*a, b, c, d*. Other data stores and data store subsystems are suitable.

Accordingly, the present invention provides an improved automated system for promoting, maintaining, and managing health and wellness.

Returning to FIG. 1, client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, BLUETOOTH™, etc.) to communicate with one another. Other electronic device/computer network architectures are suitable.

Each computer (e.g., client processor/device 50 or server computers 60) includes a system bus and a central processor unit attached to the system bus that provides for the execution of computer instructions. The system bus is a set of hardware lines used for data transfer among the components of the computer or processing system. That is, the system bus is essentially a shared conduit that connects different elements of a computer system (e.g., processor, disk storage, memory, input/output ports, network ports, etc.) that enables the transfer of information between the elements. Attached to the system bus is I/O device interface for connecting various input and output devices (e.g., keyboard, mouse, displays, printers, speakers, etc.) to the computer 50, 60. A network interface allows the computer to connect to various other devices attached to a network (e.g., network 70 of FIG. 1). Memory 90 provides volatile storage for computer software instructions and data (illustrated by various arrows) used to implement an embodiment 11 of the present invention (e.g., rewards engine 65 and respective device/sponsor data collection platforms 62 for multi-sponsor processing, voucher generation, and supporting code as detailed above). Disk storage 95 provides non-volatile storage for computer software instructions and data used to implement an embodiment of the present invention.

In one embodiment, the processor routines and data are a computer program product, including a computer readable medium (e.g., a removable storage medium, such as one or more DVD-ROM's, CD-ROM's, diskettes, tapes, etc.) that provides at least a portion of the software instructions for the invention system. Computer program product can be installed by any suitable software installation procedure, as is well known in the art. In another embodiment, at least a portion of the software instructions may also be downloaded over a cable, communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

While this invention has been particularly shown and described with references to example embodiments thereof, it will be understood by those skilled in the art that various changes in form and details may be made therein without departing from the scope of the invention encompassed by the appended claims.

What is claimed is:

1. A computer-based health, wellness, and fitness-promotion system, comprising:

in one or more computers:
   a member data store storing in memory information about members, including a respective member account per member;
   a sponsor data store storing in memory sponsor data of one or more sponsors, for each sponsor the sponsor data store indicating (i) qualifying members, (ii) qualifying healthy activities for which qualifying members are to be rewarded and (iii) reward rate for each qualifying healthy activity; and
   a rewards engine executable by a processor and responsive to input data effectively indicating qualifying healthy activity completed by a subject member, the rewards engine using the sponsor data as stored in the sponsor data store and determining number of units to add to the respective member account of the subject member for the completed healthy activity, wherein the respective member account accumulates units awarded to the subject member by one or more different sponsors for different qualifying healthy activities, said accumulating being at an increased potential due to multiple potential sponsors, thereby promoting participation in healthy activities by the members.

2. The computer-based health, wellness, and fitness promotion system as claimed in claim 1 wherein the qualifying healthy activities include qualifying healthy purchases; and
the input data include indications of the qualifying healthy purchases.

3. The computer-based health, wellness, and fitness promotion system as claimed in claim 1 wherein the input data includes file feeds from any combination of sponsors and data capture partners.

4. The computer-based health, wellness, and fitness promotion system as claimed in claim 1 wherein the input data includes point-of-sale data from sponsors.

5. The computer-based health, wellness, and fitness promotion system as claimed in claim 1 further comprising a voucher process in which:
a sponsor purchases member account units in the form of a voucher;
the sponsor issues the voucher to a member in reward for completing a sponsor-specified healthy activity; and
the member is able to redeem the voucher to credit his member account.

6. The computer-based health, wellness, and fitness promotion system as claimed in claim 1 further comprising a rebate process enabling the subject member to make a certain healthy purchase; and
the rewards engine being responsive to the certain healthy purchase and crediting to the respective member account a number of units having a value equivalent to a percentage of the purchase price.

7. The computer-based health, wellness, and fitness promotion system as claimed in claim 1 wherein the different sponsors include combinations of employer, health club, insurer, retailers, manufacturers, government entities, healthcare profession service providers, and pharmaceutical entities.

8. The computer-based health, wellness, and fitness promotion system as claimed in claim 7 wherein at least one retailer has a frequent shopper program in which the subject member participates; and
the sponsor data store cross references the subject member by a frequent shopper program identification of the subject member.

9. The computer-based health, wellness, and fitness promotion system as claimed in claim 7 wherein at least one retailer has a frequent shopper program in which the subject member participates; and
the qualifying healthy activities include purchasing healthy items for which the frequent shopper program provides certain benefits/rewards.

10. The computer-based health, wellness, and fitness promotion system as claimed in claim 1, further comprising:
a portal in communication with the member data store, the portal configured to enable a member to access his respective member account.

11. A computer method for promoting health, wellness, and fitness via a computer environment, comprising:
in a processor:
storing information about members, including a respective member account per member, in a member data store in computer memory;
storing sponsor data of one or more sponsors in a sponsor data store in computer memory, the sponsor data including indications for each sponsor of (i) qualifying members, (ii) qualifying healthy activities for which qualifying members are to be rewarded and (iii) reward rate for each qualifying healthy activity;
responding to input data that effectively indicates qualifying healthy activity completed by a subject member, said responding being by a rewards engine executed by the processor;
determining, with the rewards engine, a number of units to add to the respective member account of the subject member for healthy activity completed by a subject member using the sponsor data; and
accumulating units awarded to the subject member in the respective member account by one or more different sponsors for different qualifying healthy activities, said accumulating being at an increased potential due to multiple potential sponsors, thereby promoting participation in healthy activities by the members.

12. The computer method as claimed in claim 11 wherein storing sponsor data includes storing qualifying healthy purchases; and
responding to input data includes responding to indications of qualifying healthy purchases.

13. The method as claimed in claim 11 wherein responding to input data includes responding to file feeds from any combination of sponsors and data capture partners.

14. The method as claimed in claim 11 wherein responding to input data includes responding to point-of-sale data from sponsors.

15. The method as claimed in claim 11 further comprising:
enabling a sponsor to purchase member account units in the form of a voucher;
enabling the sponsor to issue the voucher to the subject member in reward for completing a sponsor-specified healthy activity; and
enabling the subject member to redeem the voucher to credit his member account.

16. The method as claimed in claim 11 further comprising:
enabling the subject member to receive a rebate upon making a certain healthy purchase; and
crediting to the respective member account a number of units having a value equivalent to a percentage of the purchase price with the rewards engine.

17. The method as claimed in claim 11 wherein the different sponsors include combinations of employer, health club, insurer, retailers, manufacturers, government entities, healthcare profession service providers, and pharmaceutical entities.

18. The method as claimed in claim 17 further comprising:
cross-referencing the subject member by a frequent shopper program identification of the subject member.

19. The method as claimed in claim 16 wherein the qualifying activities include purchasing healthy items for which the frequent shopper program provides certain benefits/rewards.

20. The method as claimed in claim 11, further comprising:
enabling a member to access his respective member account via a portal in communication with the sponsor data store.

* * * * *